United States Patent [19]

Fried

[11] Patent Number: 5,250,727

[45] Date of Patent: Oct. 5, 1993

[54] PREPARATION OF ALKOXYALKANOIC ACIDS

[75] Inventor: Herbert E. Fried, Houston, Tex.

[73] Assignee: Shell Oil Company, Houston, Tex.

[21] Appl. No.: 996,287

[22] Filed: Dec. 23, 1992

[51] Int. Cl.$^5$ .................... C07C 51/16; C07C 51/235; C07C 51/27; C07C 51/245

[52] U.S. Cl. .................................................. 562/540

[58] Field of Search ............... 562/540, 537, 538, 587

[56] References Cited

U.S. PATENT DOCUMENTS 5,162,579 11/1992 Fried .................................. 562/537
5,166,422 11/1992 Fried .................................. 562/537
5,166,423 11/1992 Fried .................................. 562/537
5,175,360 12/1992 Fried .................................. 562/538

*Primary Examiner*—Arthur C. Prescott
*Attorney, Agent, or Firm*—Pamela J. McCollough

[57] ABSTRACT

A process for preparing an alkoxyalkanoic acid by reacting the corresponding alkoxyalkanol with a stable free radical nitroxide in the presence of a $NO_x$-generating compound and, optionally, an oxidant and/or a solvent, at a temperature in the range of from about 0° C. to about 100° C. and thereafter separating out the alkoxyalkanoic acid.

24 Claims, No Drawings

PREPARATION OF ALKOXYALKANOIC ACIDS

FIELD OF THE INVENTION

This invention relates to a process for the preparation of alkoxyalkanoic acids by the oxidation of the corresponding alkoxyalkanols in the presence of a stable free radical nitroxide and a $NO_x$-generating compound.

BACKGROUND OF THE INVENTION

Alkoxyalkanoic acids are useful as anionic surfactants or emulsifying agents. These acids, being composed of only the elements C, H and O, do not pose the environmental problems that other detergents containing heteroatoms such as N, S, and P pose. The alkoxyalkanoic acids can be prepared in a two-step process of first reacting an alkanol with an alkoxylate and a suitable alkoxylation catalyst and thereafter converting the resultant alkoxyalkanol to the alkoxyalkanoic acid.

It is also known to convert alkoxyalkanols such as methyl carbitol to the corresponding carboxylic acids by oxidizing them with nitric acid. However, relatively large amounts of nitric acid are required and not all of the nitric acid can be separated by distillation. In addition, cleavage of the ether linkages occurs to a large degree during this process.

Japanese Patent No. 50-96516, issued Jul. 31, 1975, discloses a process for the preparation of carboxylic acid salts by the liquid phase dehydrogenation of alcohols with caustic alkali in the presence of precious metal catalysts, including palladium. This process uses a relatively high temperature, 100° C.–270° C. These high temperatures can degrade the ether linkages especially in the highly ethoxylated alcohols.

It is known to use nitroxyl radicals/oxoammonium salts in the oxidation of primary alcohols to produce aldehydes and acids and secondary alcohols to ketones. *Journal of Organic Chemistry*, vol. 52 (12), pp. 2,559–2,562; *Pure and Applied Chemistry*, vol. 62(2), 1990, pp. 217–222; *Journal of Organic Chemistry*, vol. 55, 1990, pp. 462–466. The primary products produced in these processes are aldehydes and the stoichiometrically consumed oxidant is hypochlorite.

It is generally more difficult to oxidize alkoxyalkanols than alkanols as it is difficult to oxidize alkoxyalkanols without splitting the molecular chain at the ether linkage and thereby produce a large proportion of undesired by-product. In addition, the more oxyalkylene groups there are in an alkoxyalkanol the more difficult it is to selectively oxidize. Thus, lower concentrations of the desired hydroxyl groups are present as the molecular weight increases. This consequently increases the probability of cleavage at the ether linkages.

It would therefore be advantageous to produce alkoxyalkanoic acids in high yields and with high selectivities from alkoxyalkanols having a large number of oxyalkylene groups without producing large amounts of other products such as aldehydes, esters, polyethylene glycols and fatty acids.

It has been found that alkoxyalkanoic acids can be produced in high yields and with high selectivities without forming highly corrosive, difficult to separate, side-products by using catalytic amounts of a stable free radical nitroxide and a $NO_x$-generating compound.

SUMMARY OF THE INVENTION

This invention relates to a process for the preparation of an alkoxyalkanoic acid of the formula

wherein R is an alkyl group of from 1 to about 1,000 carbon atoms, R' is hydrogen or methyl or mixtures thereof (on the individual molecule) and n is an integer greater than 12 which comprises reacting the corresponding alkoxyalkanol with a stable free radical nitroxide having the formula:

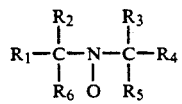

wherein (1) (a) each of $R_1$, $R_2$, $R_3$ and $R_4$ is an alkyl, aryl or heteroatom substituted alkyl group having 1 to about 15 carbon atoms, and (b) $R_5$ and $R_6$ (i) each is an alkyl group having 1 to about 15 carbon atoms provided that $R_1$–$R_6$, are not all alkyl groups, or a substituted alkyl group having 1 to about 15 carbon atoms wherein the substituent is hydrogen, cyano, —$CONH_2$, —OCOCH, $OCOC_2H_5$, carbonyl, alkenyl wherein the double bond is not conjugated with the nitroxide moiety, or —COOR wherein R of the —COOR group is alkyl or aryl, or (ii) together form part of a ring that contains 5 carbon atoms and up to two heteroatoms of O or N, or (2) the

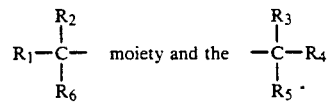

moiety individually are aryl, in the presence of a $NO_x$-generating compound at a temperature in the range of from about 0° C. to about 100° C. and thereafter separating out the alkoxyalkanoic acid.

DESCRIPTION OF THE PREFERRED EMBODIMENTS

The present process converts alkoxyalkanols of the formula

 (I)

wherein R is an alkyl group, preferably 1 to about 100; more preferably about 1 to about 20 carbon atoms, R' is hydrogen or methyl or mixtures thereof (on the individual molecule) and n represents the average number of oxyalkylene groups and is an integer greater than 12, preferably from about 20 to about 5,000, and more preferably from about 75 to about 200, to the corresponding alkoxyalkanoic acids of the formula:

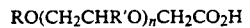 (II)

by contacting the alkoxyalkanol with a stable free radical nitroxide in the presence of a $NO_x$-generating compound and optionally, an oxidant and/or a solvent, at a temperature in the range of from about 0° C. to about 100° C. and thereafter separating out the alkoxyalkanoic acid. The alkyl group, R' in the above formula I can be substituted with any substituent which does not interfere with the oxidation of the hydroxy group. Such substituents include —OR", —CH$_3$, —COOH, CONH$_2$ and COOR" wherein R" is an alkyl or aryl group.

The process of the instant invention is particularly suited to ethoxylated, or propoxylated alcohols with alkyl chains (R) of about 1 to about 100, preferably of about 1 to about 20 carbon atoms. The R' groups on an individual molecule can be hydrogen, methyl or mixtures thereof. For example, straight ethoxylated, straight propoxylated and mixed ethoxylated-propoxylated detergent alcohols are available. The number of such alkoxylate groups, (CH$_2$CHR'O), typically ranges from about 75 to about 200. In a preferred embodiment, the starting alkoxyalkanol is an ethoxylated alcohol having about 100 ethylene oxide units per molecule.

Preferred alkoxyalkanol reactants in the present invention are poly(ethylene glycol) methyl ethers with average molecular weights of 5,000, 2,000, 750, 550 or 350, poly(ethylene glycol) ethyl ethers with average molecular weights of 5,000, 2,000, 750, 550 or 350, and poly(ethylene glycol) butyl ethers with average molecular weights of 5,000, 2,000, 750, 550 or 350.

The term "stable free radical nitroxide" as used herein shall mean a free radical nitroxide that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the precursor to a stable free radical from which the stable free radical may be produced in-situ.

The stable free radical nitroxides, as used in the present process, are precursors to catalysts, i.e., oxoammonium salts, active for the oxidation of alkanols to the corresponding acids. These catalysts are generated in situ by the oxidation of a stable free radical nitroxide to an oxoammonium salt. The stable free radical nitroxide can be obtained by the oxidation of secondary amines or hydroxylamines.

The stable free radical nitroxides which are suitable for use in the instant invention have the formula:

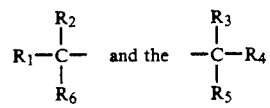
(III)

wherein (1) (a) each of $R_1$, $R_2$, $R_3$ and $R_4$ is an alkyl, aryl or heteroatom substituted alkyl group and no hydrogen is bound to the remaining valences of the carbon atoms bound to the nitrogen. As used herein the term "alkyl" is meant to include cycloalkyl. The alkyl (or heteroatom substituted) groups $R_1$–$R_4$ may be the same or different, and preferably contain 1 to 15 carbon atoms. Preferable, $R_1$–$R_4$ are methyl, ethyl, or propyl groups. In addition to hydrogen, the heteroatom substituents may include, halogen, oxygen, nitrogen and the like.

The remaining valences ($R_5$ and $R_6$) in formula III above may be satisfied by any atom or group except hydrogen which can bond covalently to carbon, although some groups may reduce the stabilizing power of the nitroxide and are undesirable. When $R_1$, $R_2$, $R_3$ and $R_4$ are each alkyl groups, however, at least one of $R_5$ and $R_6$ must be an aryl group. Preferably, $R_5$ and $R_6$ are substituted alkyl group having 1 to about 15 carbon atoms wherein the substituent is selected from hydrogen, cyano, —COOR, wherein R is alkyl or aryl, —CONH$_2$, OCOC$_2$H$_5$, carbonyl, alkenyl where the double bond is not conjugated with the nitroxide moiety, or alkyl groups of 1 to about 15 carbon atoms. $R_5$ and $R_6$ together may also form a ring of five carbon atoms and up to two heteroatoms, such as O or N. Examples of suitable compounds having the structure above and in which $R_5$ and $R_6$ form part of the ring are piperidinyl-1-oxyls and pyrrolidin-1-oxyls.

The

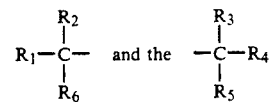

moieties in formula III above can individually be aryl, i.e.

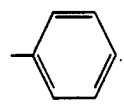

Examples of suitable compounds having the structure above in which the

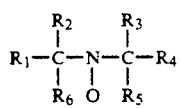

moieties are individually aryl are diphenylamine, phenyl tertiary butylamine, 3,3'-dimethyldiphenylamine, 2,2'-dichlorodiphenylamine and the like. These compounds may be substituted with an substituents which do not interfere with the reaction.

In a preferred embodiment the stable free radical nitroxide has the formula:

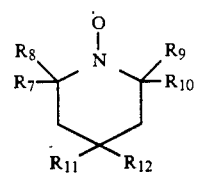

wherein each of $R_7$, $R_8$, $R_9$ and $R_{10}$ is an alkyl, aryl or heteroatom substituted alkyl group having 1 to about 15 carbon atoms and no hydrogen is bound to the remaining valences on the carbon atoms bound to the nitrogen, and each of $R_{11}$ and $R_{12}$ is alkyl, hydrogen, aryl or a substituted heteroatom. As used herein, the term "alkyl" is meant to include cycloalkyl. The alkyl (or heteroatom substituted) groups $R_7$–$R_{10}$ may be the same or different, and preferably contain 1 to 15 carbon atoms. Preferably, $R_7$–$R_{10}$ are methyl, ethyl, or propyl groups. In addition to hydrogen, the heteroatom substituents may include, halogen, oxygen, nitrogen and the like. Preferably, one of $R_{11}$ and $R_{12}$ is hydrogen, with the other one being a substituted heteroatom which does not interfere with the reaction. Suitable substituted heteroatoms include

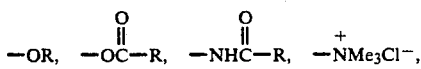

—O—SO₃H, —O— polymer and the like.

In a particularly preferred embodiment, the nitroxide is selected from the group consisting of 2,2,6,6-tetramethyl-piperidine-1-oxyl, 4-hydroxy-2, 2,6,6-tetramethyl-piperidine-1-oxyl, 2,2,6,6-tetramethylpiperidine-1-oxyl-4-sulfate, 4-alkoxy-2,2,6,6-tetramethyl-piperidine-1-oxyl, and mixtures thereof, with 2,2,6,6-tetramethyl-piperidine-1-oxyl, 2,2,6,6-tetramethyl-piperidine-1-oxyl-4-sulfate, and 4-alkoxy-2,2,6,6-tetramethyl-piperidine-1-oxyl being particularly preferred.

The NO$_x$-generating compound in the present process is typically selected from the group consisting of an alkali metal nitrosodisulfonate, nitric acid and mixtures thereof, with nitric acid being preferred. However, any compound which serves to generate NO$_x$ during the course of the reaction and which does not interfere with the reaction would be suitable. While not wishing to be bound by any particular theory, it is believed that nitrogen oxides (NO$_x$) are generated in the reaction and are required to generate the active catalytic species.

The alkali metal nitrosodisulfonate suitable for use as a NO$_x$-generating compound can be any alkali metal nitrosodisulfonate although potassium nitrosodisulfonate is preferred. As used herein, the term "alkali metal" is used as a descriptor of the elements Group IA of the Periodic Table of the Elements (Li, Na, K, Rb, Cs, Fr). The alkali metal nitrosodisulfonate is typically dissolved in water prior to being added to the reaction mixture although it can be added as a solid after all of the other reactants have been added.

As used herein, the term "nitric acid" refers to nitric acid, fuming nitric acid or nitrous acid generated by contacting alkali metal nitrite with mineral acid. Nitric acid can also be generated by contacting alkali metal nitrate with mineral acid. The nitric acid suitable for use in the present invention typically has a concentration in the range of from about 50 percent to about 100 percent, preferably about 70 percent. Generally, an amount of nitric acid in the range of from about 5 mole percent to about 1,000 mole percent, basis the moles of starting alkoxyalkanol is utilized. The nitric acid is typically added to the reaction mixture after all of the other reactants have been added.

In a preferred embodiment, an oxidant is also added as a reactant. In general, when catalytic amounts of the NO$_x$-generating compound are used, the addition of an oxidant is preferred, whereas when stoichiometric amounts of the NO$_x$-generating compound are used, an oxidant is not needed. The oxidants suitable for use in the instant invention are those compounds which are capable, in the presence of nitric acid, of oxidizing the stable free radical nitroxide to the oxoammonium salt. Suitable oxidants include oxygen-containing gases such as pure oxygen and oxygen in air. Whereas pure oxygen can is preferred to accomplish the desired conversion, the oxygen can also be diluted with an inert gas such as nitrogen, helium, argon, or other similar gas. While air can be used as the oxidant, the reaction rate is much slower. For purposes of increasing the reaction rate, higher O$_2$ pressures such as, for example, 1,000 psig can be utilized. In a preferred embodiment, pure oxygen is used as the oxidant and it is bubbled into the reaction solution.

The reaction is preferably carried out in the presence of a solvent. When the molecular weight is such that the alkoxyalkanol reactant is a solid or a viscous liquid, a solvent in which the solid or highly viscous alkoxyalkanol reactant is soluble must be added. Suitable solvents are thus those in which the alkoxyalkanol reactant is soluble and those which do not interfere with the reaction. Suitable solvents include dichloromethane, triglyme, tertiary butyl alcohol, acetonitrile, carbon tetrachloride, monoglyme, diglyme, tertiary amyl alcohol and the like, and mixtures thereof. In a preferred embodiment, the solvent is selected from the group consisting of dichloromethane, acetonitrile, tertiary butyl alcohol and mixtures thereof. The weight ratio of solvent to alkoxyalkanol reactant is typically in the range of from about 1:1 to about 1:100, and preferably in the range of from about 1:1 to about 1:5.

The amounts and concentrations of the reactants utilized in the process of the instant invention can vary within wide ranges. The amount of stable free radical nitroxide is typically in the range of from about 1 mole percent to about 500 mole percent, preferably from about 2 mole percent to about 20 mole percent, basis the number of moles starting alkoxyalkanol. Generally, the amount of nitric acid used is in the range of from about 5 mole percent to about 1,000 mole percent, basis the number of moles of alkoxyalkanol.

The process of the present invention is typically conducted under mild conditions, with good results being obtained using a temperature in the range of from about 0° C. to about 100° C., preferably about 20° C. to about 70° C., and most preferably, about 40° C. to about 60° C. Reaction pressures are not critical although higher pressures may result in increased reaction rates. Pressures in the range of from about atmospheric pressure up to about 100 psig can be employed with good results.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized and on the concentration of the nitroxide.

The process of the instant invention can be carried out in a variety of ways. For example, 0.0032 moles of alkoxyalkanol, and 0.0006 moles percent by weight of the nitroxide, may be added to the reaction vessel, followed by the addition of 0.0022 moles of 70 percent nitric acid and bubbling O$_2$ through the reaction mixture. Following the reaction, the product may be separated from the reaction mixture using conventional procedures such as for example, an extraction procedure or a precipitation procedure. The particular procedure utilized depends on whether the reaction product is a solid or liquid at room temperature. If the product is a solid at room temperature, precipitation is typically used. If, however, the product is a liquid at room temperature, an extraction procedure is generally used. The reaction product can be purified by a number of conventional means such as water washing or catalytic hydrogenation.

Depending upon process conditions and the nitroxide used, the yields of alkoxyalkanoic acid obtained by this invention can be greater than about 98% of starting material being converted. The products produced by the instant process can be used as emulsifying agents or in a variety of detergent applications.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

In the following examples, the starting alkoxyalkanol was a poly(ethylene glycol) methyl ether having a molecular weight of 5,000 which was prepared by ethoxylating methanol to an ethoxylated alcohol having about 110 ethylene oxide units per molecule.

EXAMPLE 1

16.2 Grams of the starting alkoxyalkanol, 0.1 grams of 2,2,6,6-tetramethyl-piperidine-1-oxyl, 25 milliliters of dichloromethane and 0.2 grams of 70 percent nitric acid were charged to a 100 milliliter round bottomed flask. To this mixture was added $O_2$. The reaction temperature was held at 40° C. over a 3-hour period. The results are presented in Table I.

EXAMPLE 2

16.2 Grams of the starting alkoxyalkanol, 1 gram of 2,2,6,6-tetramethyl-piperidine-1-oxyl, 1 gram of Aliquot 336, 25 milliliters of tertiary butyl alcohol and 1 gram of 70 percent nitric acid were charged to a 100 milliliter round bottomed flask. To this mixture was added $O_2$. The reaction was held at 50° C. over a 6-hour period. The results are presented in Table I.

EXAMPLE 3

100 Grams of the starting alkoxyalkanol, 6.25 grams of 2,2,6,6-tetramethyl-piperidine-1-oxyl, 200 milliliters of acetonitrile, and 6.25 grams of 70 percent nitric acid were charged to a 350 milliliter glass vessel. Air was then sparged through the reaction vessel. The reaction temperature was held at 60° C. over a 4-hour period. The results are presented in Table I.

COMPARATIVE EXAMPLE A

Comparative Example A was carried out in a manner similar to Example 1 except that no nitroxide was used. The results are presented in Table I.

COMPARATIVE EXAMPLE B

Comparative Example B was carried out in a manner similar to Example 1 except that no nitric acid was used. The results are presented in Table I.

As can be seen in Table I, nitroxide and nitric acid are necessary for the oxidation of the alkoxyalkanol to proceed.

TABLE I

| Oxidation Of Alkoxyalkanols to Alkoxyalkanoic Acids | | |
|---|---|---|
|  | % Conversion | % Selectivity to Acids |
| Example 1 | >99 | >99 |
| Example 2 | >99 | >99 |
| Example 3 | >99 | >99 |
| Comparative Example A | 0 | 0 |
| Comparative Example B | 0 | 0 |

What is claimed is:

1. A process for the preparation of an alkoxyalkanoic acid of the formula $$RO(CH_2CHR'O)_nCH_2CO_2H$$

wherein R is an alkyl group of from 1 to about 1,000 carbon atoms, R' is hydrogen or methyl or mixtures thereof (on the individual molecule) and n is an integer greater than 12, which comprises reacting the corresponding alkoxyalkanol with a stable free radical nitroxide having the formula:

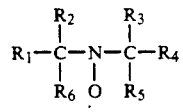

wherein (1) (a) each of $R_1$, $R_2$, $R_3$ and $R_4$ is an alkyl, aryl or heteroatom substituted alkyl group having 1 to about 15 carbon atoms, and (b) $R_5$ and $R_6$ (i) each is an alkyl group having 1 to about 15 carbon atoms provided that $R_1$–$R_6$, are not all alkyl groups, or a substituted alkyl group having 1 to about 15 carbon atoms wherein the substituent is hydrogen, cyano, —$CONH_2$, —OCOCH, $OCOC_2H_5$, carbonyl, alkenyl wherein the double bond is not conjugated with the nitroxide moiety, or —COOR wherein R of the —COOR group is alkyl or aryl, or (ii) together form part of a ring that contains 5 carbon atoms and up to two heteroatoms of O or N, or (2) the

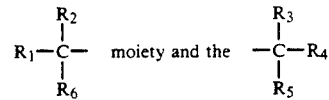

moiety individually are aryl, in the presence of a $NO_x$-generating compound at a temperature in the range of from about 0° C. to about 100° C. and thereafter separating out the alkoxyalkanoic acid.

2. The process of claim 1 wherein n is an integer in the range of from about 20 to about 5,000.

3. The process of claim 2 wherein n is an integer in the range of from about 75 to about 200.

4. The process of claim 1 wherein the stable free radical nitroxide has the formula:

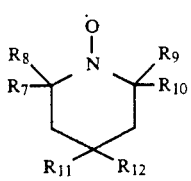

wherein each of $R_7$, $R_8$, $R_9$ and $R_{10}$ is an alkyl, aryl or heteroatom substituted alkyl group having 1 to about 15 carbon atoms and each of $R_{11}$ and $R_{12}$ is alkyl, hydrogen, aryl or a substituted heteroatom.

5. The process of claim 4 wherein the stable free radical nitroxide is selected from the group consisting of 2,2,6,6-tetramethylpiperidine-1-oxyl, 4-hydroxy-2,2,6,6-tetramethyl-piperidine-1-oxyl, 4-alkoxy-2,2,6,6-tetramethyl-piperidine-1-oxyl, 2,2,6,6-tetramethyl-piperidine-1-oxyl-4-sulfate and mixtures thereof.

6. The process of claim 5 wherein the stable free radical nitroxide is selected from the group consisting of 2,2,6,6-tetramethylpiperidine-1-oxyl, 2,2,6,6-tetramethyl-piperidine-1-oxyl-4-sulfate, 4-alkoxy-2,2,6,6-tetramethyl-piperidine-1-oxyl and mixtures thereof.

7. The process of claim 1 wherein said $NO_x$-generating compound is selected from the group consisting of nitric acid, an alkali metal nitrosodisulfonate and mixtures threof.

8. The process of claim 7 wherein said $NO_x$-generating compound is nitric acid.

9. The process of claim 8 wherein said nitric acid is selected from the group consisting of fuming nitric acid, nitrous acid generated by contacting an alkali metal nitrite with mineral acid, nitric acid generated by contacting an alkali metal nitrate with mineral acid, and mixtures thereof.

10. The process of claim wherein said nitric acid has a concentration in the range of from about 50 percent to about 100 percent.

11. The process of claim 9 wherein the amount of nitric acid is in the range of from about 5 mole percent to about 1,000 mole percent, basis the number of moles alkoxyalkanol.

12. The process of claim 7 wherein said $NO_x$-generating compound is an alkali metal nitrosodisulfonate.

13. The process of claim 12 wherein said alkali metal nitrosodisulfonate is potassium nitrosodisulfonate.

14. The process of claim 1 wherein said alkoxyalkanol is contacted with said stable free radical nitroxide, followed by the addition thereto of said $NO_x$-generating compound and said oxidant.

15. The process of claim 14 wherein the amount of stable free radical nitroxide is in the range of from about 1 mole percent to about 500 mole percent, basis the number of moles of alkoxyalkanol.

16. The process of claim 15 wherein the amount of stable free radical nitroxide is in the range of from about 5 mole percent to about 20 mole percent, basis the number of moles of alkoxyalkanol.

17. The process of claim 14 wherein the amount of $NO_x$-generating compound is in the range of from about 5 mole percent to about 1,000 mole percent, basis the number of moles of alkoxyalkanol.

18. The process of claim 1 wherein said process additionally contains an oxidant.

19. The process of claim 18 wherein said oxidant is an oxygen-containing gas.

20. The process of claim 19 wherein said oxygen-containing gas is selected from the group consisting of pure oxygen and air.

21. The process of claim 20 wherein said oxygen-containing gas is pure oxygen.

22. The process of claim 1 wherein said process is carried out in the presence of a solvent.

23. The process of claim 22 wherein said solvent is selected from the group consisting of dichloromethane, triglyme, tertiary butyl alcohol, acetonitrile, carbon tetrachloride, monoglyme, diglyme, tertiary amyl alcohol and mixtures thereof.

24. The process of claim 1 wherein said process is carried out at a temperature in the range of from about 20° C. to about 70° C. and at atmospheric pressure.

* * * * *